(12) United States Patent
Coppernoll et al.

(10) Patent No.: US 9,296,765 B2
(45) Date of Patent: *Mar. 29, 2016

(54) METHOD OF PREPARING AN ORGANOHALOSILANE

(71) Applicant: Dow Corning Corporation, Midland, MI (US)

(72) Inventors: Aaron Coppernoll, Crestwood, KY (US); Catharine Horner, Carrollton, KY (US); Krishna Janmanchi, Union, KY (US); Dimitris Katsoulis, Midland, MI (US); Robert Larsen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/419,967

(22) PCT Filed: Aug. 13, 2013

(86) PCT No.: PCT/US2013/054611
§ 371 (c)(1),
(2) Date: Feb. 6, 2015

(87) PCT Pub. No.: WO2014/028417
PCT Pub. Date: Feb. 20, 2014

(65) Prior Publication Data
US 2015/0158890 A1    Jun. 11, 2015

Related U.S. Application Data

(60) Provisional application No. 61/682,362, filed on Aug. 13, 2012.

(51) Int. Cl.
*C07F 7/12* (2006.01)
*C08G 77/04* (2006.01)

(52) U.S. Cl.
CPC ............. *C07F 7/122* (2013.01); *C08G 77/04* (2013.01)

(58) Field of Classification Search
None
See application file for complete search history.

(56) References Cited

U.S. PATENT DOCUMENTS

| | | |
|---|---|---|
| 2,380,996 A | 8/1945 | Rochow et al. |
| 2,403,370 A | 7/1946 | Hurd |
| 2,406,605 A | 8/1946 | Hurd |
| 2,458,703 A | 1/1949 | Hatcher, David B. |
| 2,595,620 A | 5/1952 | Wagner et al. |
| 2,888,476 A | 5/1959 | Little et al. |
| 3,057,686 A | 10/1962 | Muetterties |
| 4,053,495 A | 10/1977 | Deinhammer et al. |
| 4,059,608 A | 11/1977 | Calas et al. |
| 4,079,071 A | 3/1978 | Neale |
| 4,314,908 A | 2/1982 | Downing et al. |
| 4,526,769 A | 7/1985 | Ingle et al. |
| 4,602,101 A | 7/1986 | Halm et al. |
| 4,836,997 A | 6/1989 | Lepage et al. |
| 4,864,044 A | 9/1989 | Lewis et al. |
| 4,888,435 A | 12/1989 | Chadwick et al. |
| 4,946,980 A | 8/1990 | Halm et al. |
| 4,956,326 A | 9/1990 | Yoneda et al. |
| 4,973,725 A | 11/1990 | Lewis et al. |
| 4,985,580 A | 1/1991 | Chadwick et al. |
| 5,336,799 A | 8/1994 | Kalchauer et al. |
| 5,646,326 A | 7/1997 | Schuler |
| 5,716,590 A | 2/1998 | Roewer et al. |
| 6,156,380 A | 12/2000 | Aramata et al. |
| 6,211,284 B1 | 4/2001 | Ishikawa et al. |
| 6,251,057 B1 | 6/2001 | Jung et al. |
| 6,326,452 B1 | 12/2001 | Berrier et al. |
| 6,506,923 B2 | 1/2003 | Inukai et al. |
| 6,576,588 B2 | 6/2003 | Ryu et al. |
| 6,632,956 B2 | 10/2003 | Tsukuno et al. |
| 6,790,749 B2 | 9/2004 | Takemura et al. |
| 6,887,448 B2 | 5/2005 | Block et al. |
| 7,056,484 B2 | 6/2006 | Bulan et al. |
| 7,208,617 B2 | 4/2007 | Gammie |
| 7,212,778 B2 | 5/2007 | Hisakuni |
| 7,223,879 B2 | 5/2007 | Buchwald et al. |
| 7,355,060 B2 | 4/2008 | Ogawa et al. |
| 7,442,824 B2 | 10/2008 | Paetzold et al. |
| 7,559,969 B2 | 7/2009 | Sanjurjo et al. |
| 7,638,498 B2 | 12/2009 | Escher et al. |
| 7,716,590 B1 | 5/2010 | Nathan |
| 7,728,176 B2 | 6/2010 | Masaoka et al. |
| 7,754,175 B2 | 7/2010 | Bill, Jr. et al. |
| 8,124,809 B2 | 2/2012 | Masaoka et al. |

(Continued)

FOREIGN PATENT DOCUMENTS

| CN | 1209823 A | 3/1999 |
|---|---|---|
| CN | 1403372 A | 3/2003 |

(Continued)

OTHER PUBLICATIONS

Hurd, et. al., "The Vapor Phase Alkylation and Hydrogenation of Chlorosilanes", J. Am. Chem. Soc., 1945, 67 (9), pp. 1545-1548.
Eaborn, C. et al., Further studies on reactions of organic halides with disilanes catalysed by transition metal complexes, Journal of Organometallic Chemistry, vol. 225, 1982, pp. 331-341.
Golubtsov, S.A. et al., Role of the Products of Partial Chlorination of Silicon in the Formation of Methyltrichlorosilane, Russian Chemical Bulletin, vol. 21, No. 3 (1972), pp. 584-586.
H. Walter, Mechanism of the silicide-catalysed hydrodehalogenation of silicon tetrachloride to trichlorosilane, J. Chem. Soc., Faraday Trans., 1996,92, 4605-4608.

(Continued)

*Primary Examiner* — Marc Zimmer
(74) *Attorney, Agent, or Firm* — Catherine U. Brown

(57) ABSTRACT

The application relates to a method for preparing organohalosilanes in a two-step process: Steps (i) contacting a copper catalyst with hydrogen gas and halogenated silanes forming a silicon-containing copper catalyst; and Step (ii) contacting said silicon-containing copper catalyst with an organohalide to form the organohalosilane.

18 Claims, 1 Drawing Sheet

(56) References Cited

U.S. PATENT DOCUMENTS

| | | | |
|---|---|---|---|
| 8,519,207 | B2 | 8/2013 | Armbruester et al. |
| 8,697,900 | B2 | 4/2014 | Anderson et al. |
| 8,772,525 | B2 | 7/2014 | Katsoulis et al. |
| 8,865,927 | B2 * | 10/2014 | Katsoulis et al. ............ 556/478 |
| 2002/0044904 | A1 | 4/2002 | Bulan et al. |
| 2003/0220514 | A1 | 11/2003 | Lewis et al. |
| 2004/0022713 | A1 | 2/2004 | Bulan et al. |
| 2005/0074387 | A1 | 4/2005 | Bulan et al. |
| 2006/0165580 | A1 | 7/2006 | Lipshutz |
| 2009/0035205 | A1 | 2/2009 | Bohmhammel et al. |
| 2014/0178283 | A1 | 6/2014 | Schladerback et al. |
| 2014/0212352 | A1 | 7/2014 | Onal et al. |
| 2014/0322121 | A1 | 10/2014 | Dassel |

FOREIGN PATENT DOCUMENTS

| | | | |
|---|---|---|---|
| CN | 101479192 A | | 7/2009 |
| DE | 3024319 | | 1/1982 |
| DE | 4041644 A1 | | 6/1992 |
| DE | 19654154 | | 6/1997 |
| EP | 0146148 A1 | | 6/1985 |
| JP | S28-000669 | | 2/1953 |
| JP | H02-256688 A | | 10/1990 |
| JP | 2009111202 | | 5/2009 |
| WO | WO 2011/149593 | * | 12/2011 |
| WO | 2014028417 A2 | | 2/2014 |
| WO | 2014062255 A1 | | 4/2014 |

OTHER PUBLICATIONS

Juszczyk et al., of Pd/SiO2 catalysts during high temperature reduction., Department of Catalysis on Metals, Institute of Physical Chemistry, Polish Academy of Sciences, Warsaw, Pol. Catalysis Letters (2002), 78(1-4), 95-98.

Juszczyk et al., Transformation of Pd/SiO2 into palladium silicide during reduction at 450° and 500° C., Institute of Physical Chemistry, Department of Catalysis on Metals, Polish Academy of Sciences, Warsaw, Pol. Journal of Catalysis (2003), 220(2), 299-308.

Lobusevich, N.P. et al., Reactions During Direct Synthesis of Alkylchlorosilanes., vol. 48, No. 11, 1978, pp. 2534-2541.

Moreno-Manas, Marcial et al., Formation of Carbon-Carbon Bonds under Catalysis by Transition-Metal Nanoparticles, Department of Chemistry, Universitat Autonoma de Barcelona, Barcelona, Spain. Accounts of Chemical Research (2003), 36(8), 638-643.

Beccalli, Egle M., et al., C-C, C-O, C-N Bond Formation on sp2 Carbon by Palladium(II)-Catalyzed Reactions Involving Oxidant Agents., Istituto di Chimica Organica A. Marchesini, Facolta di Farmacia, Universita di Milano, Milan, Italy. Chemical Reviews (Washington, DC, United States) (2007), 107(11), 5318-5365.

Methivier, et al., Pd/SiC catalysts. Characterization and catalytic activity for the methane total oxidation.. Institut de Recherches sur la Catalyse-Cnrs, conventionne a l'Universite Claude Bernard Lyon 1, Villeurbanne, Fr. Journal of Catalysis (1998), 173(2), 374-382.

Srebowata, A. et al., Hydrodechlorination of 1,2-dichloroethane over differently reduced Pd/SiO2 catalysts., Institute of Physical Chemistry, Polish Academy of Sciences, Warsaw, Pol. Polish Journal of Chemistry (2003), 77(12).

Tanaka, Miyoko et al., Nanomaterials Laboratory, National Institute for Materials Science, Tsukuba, Sakura, Japan. Journal of Crystal Growth (2002), 237-239(Pt. 1), 254-258.

Terao, Jun et al., Transition metal-catalyzed C-C bond formation reactions using alkyl halides., Department of Applied Chemistry and Center for Atomic and Molecular Technologies, Graduate School of Engineering, Osaka University, 2-1 Yamadaoka, Suita, Osaka, Japan. Bulletin of the Chemical Society of Japan (2006), 79(5), 663-672.

Vijh, A. K. et al., Discovery of some new stable electrocatalytic materials for the anodic oxidation of hydrazine., Inst. Rech. Hydro-Quebec, Varennes, QC, Can. Journal of Materials Science Letters (1993), 12(2), 113-15.

Vijh, A. K. et al., Electrochemical activity of silicides of some transition metals for the hydrogen evolution reaction in acidic solutions., International Journal of Hydrogen Energy (1990), 15(11), 789-94.

Yin, Lunxiang, et al., Carbon-carbon coupling reactions catalyzed by heterogeneous palladium catalysts., Institute fuer Chemie, Humboldt-Universitaet Berlin, Berlin, Germany. Chemical Reviews (Washington, DC, United States) (2007), 107(1), 133-173.

Mulla, et. al., "Reaction of Magnesium Silicide & Silicon Tetrachloride/Trichlorosilane in Presence of Hydrogen", Indian Journal of Chemistry, Sep. 1988, pp. 756-758, vol. 27A.

Acker, et. al., "Reactivity of Intermetallic Compounds: A Solid State Approach to Direct Reactions of Silicon", J. Phys. Chem., 2002, pp. 5105-5117, vol. 106, Freiberg, Germany.

Acker, et. al., "Thermodynamic assessment of the copper catalyzed direct synthesis of methylchlorosilanes", Journal of Organometallic Chemistry, 2008, pp. 2483-2493, vol. 693, Freiberg, Germany.

Ding, et. al., "CuCl-Catalyzed Hydrogenation of Silicon Tetrachloride in the Presence of Silicon: Mechanism and Kinetic Modeling", American Chemical Society, Industrial & Engineering Chemistry Research, Oct. 2, 2014, pp. AK, Shanghai, China.

Wu Shengquan, Comprehensive Use of Methyltrichlorosilane, Silicone Material, Jan. 22, 2000, vol. 14, Series 1, pp. 23-25.

Song Aijun et al., Introduction of the Properties, Application and Production of Trichlorosilane, China Chlor-Alkali, Dec. 15, 2002, Series 12, pp. 40-41.

Yu Jiankun, Progress on Trichlorosilane Preparation and Refinement Techniques, Inorganic Chemicals Industry, Jan. 10, 2007, vol. 39, Series 1, pp. 14-18.

Yiqian Jiang et al., Synthesis of Trimethylchlorosilane by [BMIM]Cl-nAlCl3 Ionic Liquids-Catalyzed Redistribution between Methyltrichlorosilane and Low-Boiling Products from the Direct Synthesis of Methylchlorosilanes, Ind. Eng. Chem. Res., Jan. 6, 2011, vol. 50, pp. 1893-1898.

Tan Jun et al., Progress of Studies on the Comprehensive Utilization of Methyltrichlorosilane by Disproportionation and Transformation, Bulletin of Science and Technology, No. 2, vol. 22.

* cited by examiner

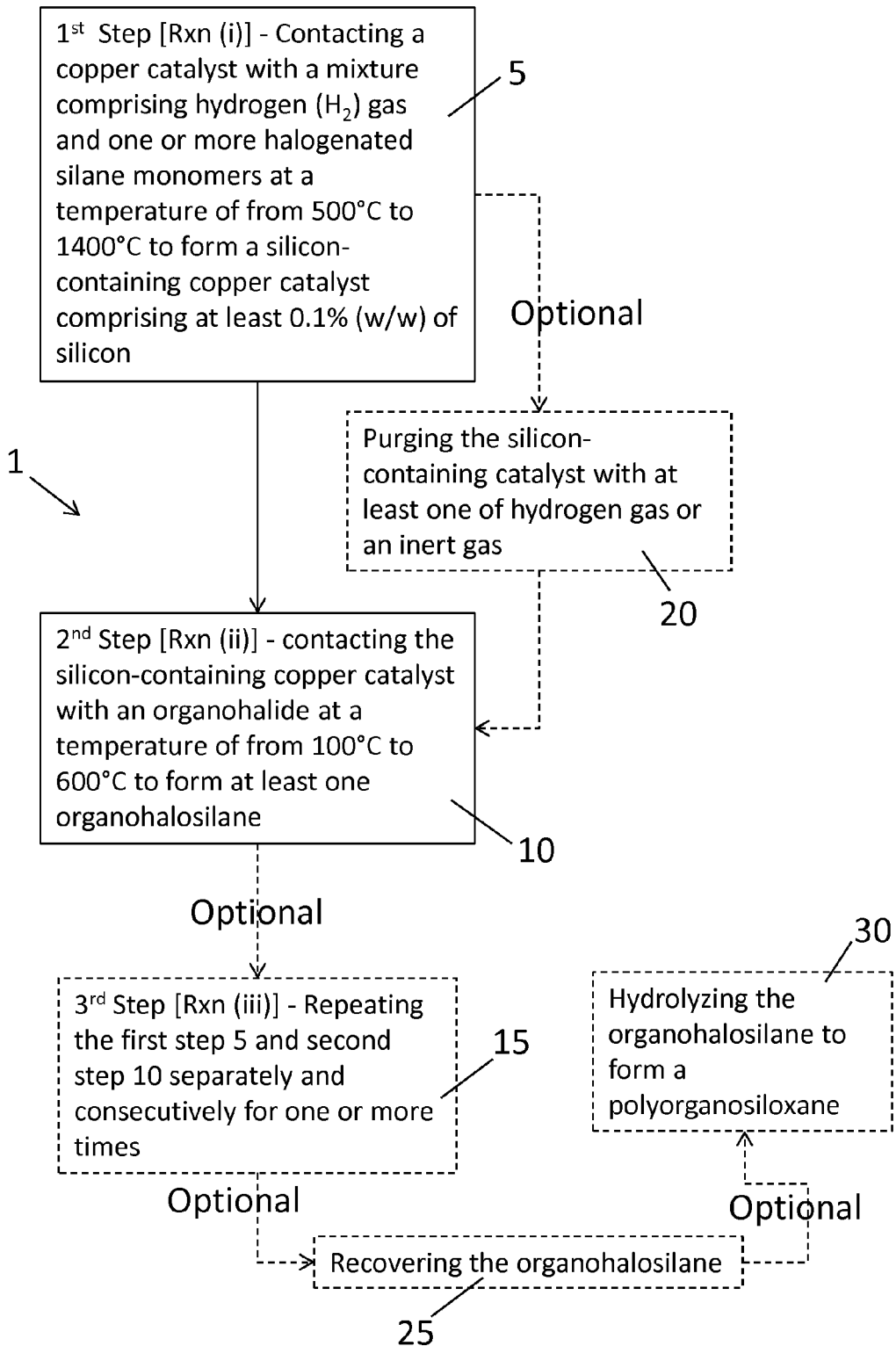

METHOD OF PREPARING AN ORGANOHALOSILANE

CROSS REFERENCE TO RELATED APPLICATIONS

This application is a U.S. national stage filing under 35 U.S.C. §371 of PCT Application No. PCT/US13/054611 filed on Aug. 13, 2013, currently pending, which claims the benefit of U.S. Provisional Patent Application No. 61/682,362 filed Aug. 13, 2012 under 35 U.S.C. §119 (e). PCT Application No. PCT/US13/054611 and U.S. Provisional Patent Application No. 61/682,362 are hereby incorporated by reference.

The present disclosure generally relates to a method of preparing an organohalosilane. More specifically, this disclosure relates to the preparation of an organohalosilane according to a method that comprises the separate and consecutive steps of (i) contacting a copper catalyst with a mixture of hydrogen gas and one or more halogenated silane monomers to form a silicon-containing copper catalyst, and (ii) contacting the silicon-containing copper catalyst with an organohalide to form at least one organohalosilane.

Statements made in this section merely provide background information related to the present disclosure and may not constitute prior art. A wide range of polyorganosiloxanes, which can be sold into various different industries and markets, are produced via the hydrolysis of organohalosilanes. Typically, these organohalosilanes are commercially made using the Mueller-Rochow Direct Process, which comprises passing an organohalide, such as methyl chloride over zero-valent silicon in the presence of a copper catalyst and various promoters to produce a mixture of organohalosilanes. This mixture of organohalosilanes is then purified and/or separated into individual components. Dimethyldichlorosilane is one example of an organohalosilane that is produced using this Mueller-Rochow Direct Process.

The conventional process used to make zero-valent silicon comprises the carbothermic reduction of $SiO_2$ in an electric arc furnace at extremely high temperatures. In this process, the generation of extremely high temperatures requires the input of significant amounts of energy, which ultimately adds substantial cost to the manufacturing of zero-valent silicon. The high cost associated with producing zero-valent silicon adds to the overall production cost associated with manufacturing organohalosilanes.

In addition to the Mueller-Rochow Direct Process, diorganodihalosilanes have been produced by the alkylation of silicon tetrachloride and various methylchlorosilanes by passing the vapors of these chlorosilanes together with an alkyl halide over finely divided aluminum or zinc at elevated temperatures. However, this process results in the production of a large amount of aluminum chloride or zinc chloride by-products, which are costly to dispose of on a commercial scale. The disposal of such by-products also adds to the production cost associated with producing organohalosilanes, such as diorganodihalosilanes.

The development of alternative methods for forming organohalosilanes that address one or more of the issues associated with the conventional process(es) described above are continually desirable. Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way.

FIG. 1 is a schematic representation of a method used to form organohalosilanes according to the teachings of the present disclosure.

BRIEF SUMMARY OF THE INVENTION

The method of the present disclosure generally uses halogenated silane monomers to produce at least one organohalosilane. Since many halogenated silane monomers are either a by-product of other industrial processes or produced using less energy than required to form zero-valent silicon, the method of the present disclosure offers multiple benefits. For example, the use of this method may be more economical than the conventional processes used to produce organohalosilanes. Alternatively, the use of this method does not produce large amounts of metal halide by-products that require costly disposal. In addition, the method of the present disclosure provides better selectivity with respect to forming more valuable diorganodihalosilanes in comparison to other organosilanes. The diorganodihalosilane produced by the method of the present disclosure can be hydrolyzed using any process known in the art capable of producing polyorganosiloxanes for subsequent use in a variety of industries and applications.

The method of the present disclosure comprises two separate and consecutive steps. The first step, Rxn (i), includes contacting a copper catalyst with a mixture that comprises hydrogen ($H_2$) gas and one or more halogenated silane monomers at a temperature of from about 500° C. to about 1400° C. to form a silicon-containing copper catalyst comprising at least 0.1% (w/w) of silicon. The second step, Rxn (ii), includes contacting the silicon-containing copper catalyst with an organohalide at a temperature of from about 100° C. to about 600° C. to form at least one organohalosilane. Alternatively the organohalosilane is a diorganodihalosilane.

The halogenated silane monomers used in Rxn (i) of this method include $RSiX_3$, $HSiX_3$, or a mixture thereof; and optionally with $SiX_4$ being added thereto, such that R is an alkyl group having between 1 to about 10 carbon atoms and X is independently selected as a chloro, bromo, fluoro, or iodo group. Alternatively, X is a chloro group with the optional $SiX_4$ added as part of the halogenated silane monomers being silicon tetrachloride. Alternatively, R is a methyl group. The mole ratio of hydrogen gas to halogenated silane monomers used in the method, including any optional $SiX_4$ as part of the halogenated silane monomers, ranges from 10:1 to 1:1.

The copper catalyst used in Rxn (i) of this method is comprised of copper or a mixture of copper and at least one element selected from gold, magnesium, calcium, cesium, tin, nickel, and sulfur; alternatively the copper catalyst is a mixture of copper and nickel. The copper catalyst may optionally include a metal oxide or carbon-based support; alternatively the support is activated carbon. One skilled in the art will understand that the copper catalyst may include impurities or various amounts of other metal or non-metal elements, including but not limited to silicon, without exceeding the scope of the present disclosure. For example, the copper catalyst may be a copper silicide catalyst previously exposed to Rxn (ii) that is being regenerated according to an optional third process step Rxn (iii) as described hereafter or the catalyst may be derived from another metal silicide. The unsupported copper catalyst generally comprises copper in an amount ranging between 0.1 to about 100% (w/w) of the total weight of the catalyst. The silicon-containing copper catalyst formed in Rxn (i) generally comprises from about 1% to about 45% (w/w) of silicon based on the total weight of the silicon-containing copper catalyst.

According to another aspect of the present disclosure, the residence time of the copper catalyst being in contract with the hydrogen gas and halogenated silane monomers is from about 0.1 second to about 45 minutes. The temperature at which the hydrogen gas and halogenated silane monomers contact the copper catalyst is between about 500° C. and about 950° C.

The organohalide used in Rxn (ii) of the method has the general formula R'X', where R' is a $C_1$-$C_{10}$ alkyl group or a $C_4$-$C_{10}$ cycloalkyl group, and X' is a chloro, bromo, fluoro, or iodo group. Alternatively, R' is a methyl group and X' is a chloro group.

The method may further comprise a third step Rxn (iii) in which the separate and consecutive Rxn (i) and Rxn (ii) are repeated one or more times. Optionally, the method may also comprise purging the silicon-containing copper catalyst formed in Rxn (i) with at least one of hydrogen gas or an inert gas prior to contacting said catalyst with the organohalide in Rxn (ii). Alternatively, the silicon-containing copper catalyst is first purged with hydrogen gas and then subsequently purged with an inert gas.

According to one aspect of the present disclosure, the organohalosilane formed using the method of the present disclosure may be a diorganodihalosilane having the formula $R''_2SiX''_2$, where R'' is a $C_1$-$C_{10}$ alkyl group or a $C_4$-$C_{10}$ cycloalkyl group, and X'' is a fluoro, chloro, bromo, or iodo group. Alternatively, R'' is a methyl group and X'' is a chloro group. Alternatively, the organohalosilane is a mixture of various organohalosilanes that can be separated or purified if desired. Thus according to another aspect of the present disclosure, the method may further comprise the step of recovering the organohalosilane or alternatively the diorganodihalosilane.

Further areas of applicability will become apparent from the description provided herein. It should be understood that the description and specific examples are intended for purposes of illustration only and are not intended to limit the scope of the present disclosure.

DETAILED DESCRIPTION

The following description is merely exemplary in nature and is in no way intended to limit the present disclosure or its application or uses. It should be understood that throughout the description, corresponding reference numerals indicate like or corresponding parts and features.

The present disclosure provides a method of preparing at least one organohalosilane. This method generally comprises the use of at least two separate and consecutive steps. Referring to FIG. 1, the first step 5 in the method 1, which is also referred to as Rxn (i), includes contacting a copper catalyst with a mixture that comprises hydrogen ($H_2$) gas and one or more halogenated silane monomers at a temperature of from about 500° C. to 1400° C. to form a silicon-containing copper catalyst comprising at least 0.1% (w/w) of silicon. The second step 10, which is also referred to as Rxn (ii), includes contacting the silicon-containing copper catalyst formed in Rxn (i) with an organohalide at a temperature of from about 100° C. to about 600° C. to form at least one organohalosilane, alternatively at least one diorganodihalosilane.

The copper catalyst is comprised of copper or a mixture of copper and at least one element selected from gold, magnesium, calcium, cesium, tin, nickel, and sulfur. Alternatively, the copper catalyst is a mixture of copper and nickel. One skilled in the art will understand that the copper catalyst may include impurities or various amounts of other metal or non-metal elements, including but not limited to silicon, without exceeding the scope of the present disclosure. For example, the copper catalyst may be a silicon-containing catalyst previously exposed to Rxn (ii) that is being regenerated according to an optional third process step Rxn (iii) as described hereafter or the catalyst may be derived from a metal silicide, including but not limited to a copper silicide. The copper catalyst may optionally include a metal oxide or carbon-based support; alternatively an activated carbon support. In other words, the copper catalyst can be a supported or unsupported catalyst. Examples of supports include, but are not limited to, oxides of aluminum, titanium, zirconium, and silicon; activated carbon; carbon nanotubes; fullerenes; and other allotropic forms of carbon. According to one aspect of the present disclosure, the support is activated carbon.

The unsupported copper catalyst typically comprises from 0.1% to about 100% (w/w) of copper, based on the total weight of the catalyst. Alternatively, the unsupported copper catalyst comprises from 0.1% to about 80% (w/w); alternatively from about 1% to 80% (w/w); alternatively, from about 10% to about 80% (w/w); alternatively, from about 40% to about 80% (w/w) of copper based on the total weight of the catalyst When the copper catalyst includes a support, the catalyst typically comprises from 0.1 to less than 100% (w/w), alternatively from 0.1 to about 80% (w/w); alternatively from 0.1 to about 50% (w/w), alternatively from 0.1 to about 35% (w/w), of copper or the metal mixture, based on the combined weight of the support and copper or the metal mixture.

The copper catalyst can take any physical form known to one skilled in the art including, but not limited to, lumps, granules, flakes, powder, and nanoparticles. Several specific examples of unsupported copper catalysts include, but are not limited to, metallic copper; mixtures of metallic copper and metallic nickel; mixtures of metallic copper and metallic gold; mixtures of metallic copper, metallic gold and magnesium chloride; mixtures of metallic copper, metallic gold and sulfur; mixtures of metallic copper and tin; mixtures of metallic copper and cesium; and mixtures of metallic copper and calcium chloride. As used herein, the term "metallic" means that the metal has an oxidation number of zero. Several specific examples of supported copper catalysts include, but are not limited to, the unsupported copper catalysts described above dispersed within an activated carbon support.

The unsupported and supported copper catalysts of the present disclosure can be made by any process known to one skilled in the art. For example, one process of making the unsupported catalyst includes mixing the various metals together to form the copper catalyst. Alternatively, metal salts including, but not limited to, halide, acetate, nitrate, and carboxylate salts, may be first mixed in predetermined or desired proportions and then be subsequently subjected to a known reduction process. One such reduction process is described below as a specific example, among others to demonstrate the preparation of a supported copper catalyst. This process may leave some salts, such as magnesium chloride, unreduced, while reducing others.

The supported copper catalyst may be prepared by, for example, combining a copper salt, such as cupric chloride, in a solvent, such as water or acid, applying the mixture to a support, and reducing the copper salt on the surface of the support. For example, $CuCl_2$ can be dissolved in water or hydrochloric acid and mixed with activated carbon. Excess $CuCl_2$ solution can then be removed, and the activated carbon-$CuCl_2$ mixture dried. The $CuCl_2$ can then be reduced on the activated carbon support with hydrogen at 500° C. to give a supported copper catalyst. One skilled in the art would understand that the steps of adding the metallic salts followed by subsequent reduction can each be carried out as a single step or involve a multiple step process without exceeding the scope of the present disclosure. Additional examples of making unsupported and supported copper catalysts are provided in the examples described herein, as well as in co-pending International Patent Application No. PCT/US2011/030683, as filed on Mar. 31, 2011, the entire contents of which are hereby incorporated by reference.

The halogenated silane monomers include $RSiX_3$, $HSiX_3$, or a mixture thereof; and optionally with $SiX_4$ being added thereto, such that R is an alkyl group having between 1 to 10 carbon atoms and X is independently selected as a chloro, bromo, fluoro, or iodo group. Alternatively R is a methyl or ethyl group and X is a chloro or bromo group. Several examples of halogenated silane monomers include, but are not limited to trichlorosilane, tribromosilane, methyltrichlorosilane, methyltribromosilane, ethyltrichlorosilane, ethyltribromosilane, or mixtures thereof. Several examples of the optional silicon tetrahalide, $SiX_4$, that may be included as part of the halogenated silane monomers are silicon tetrachloride, silicon tetrabromide, silicon tetraiodide, and silicon tetrafluoride; alternatively the silicon tetrahalide is silicon tetrachloride. The mole ratio of hydrogen to the halogenated silane monomers, including any optional silicon tetrahalide present, that is allowed to contact the copper catalyst ranges from 10,000:1 to 0.01:1, alternatively from about 100:1 to 0.1:1, alternatively from about 20:1 to about 1:1, alternatively from about 10:1 to about 1:1.

The reactor system used in the first step 5, i.e., Rxn (i), of the method 1 may include any reactor known to one skilled in the art that is suitable for combining and reacting a gas with a solid material. For example, suitable reactor configurations include, but are not limited to, a packed bed, a stirred bed, a vibrating bed, a moving bed, a re-circulating bed, or a fluidized bed. When using a re-circulating bed, the silicon-containing copper catalyst can be circulated from a first bed used to perform Rxn (i) to a second bed used for conducting Rxn (ii). When desirable to facilitate or control the reaction, the reactor system may include a means to control the temperature of the reaction. The temperature at which the hydrogen gas and halogenated silane monomers make contact with the copper catalyst can range from about 500° C. to 1400° C.; alternatively from about 500° C. to about 1200° C.; alternatively from about 500° C. to about 950° C. The pressure at which the hydrogen gas and halogenated silane monomers make contact with the copper catalyst can be sub-atmospheric, atmospheric, or super-atmospheric. For example, the pressure may range from about 100 to 2000 kilopascals gauge (kPag); alternatively from about 100 to about 1000 kPag; alternatively from about 100 to about 800 kPag, at a temperature from about 500° C. to 1400° C. The hydrogen gas and halogenated silane monomers may be fed into the reactor simultaneously; however, other methods of combining, such as by separate pulses, are also envisioned to be within the scope of the present disclosure.

The residence time for copper catalyst to be in contact with the hydrogen and halogenated silane monomers is predetermined such that it is sufficient to form the silicon-containing copper catalyst. For example, a sufficient residence time for the copper catalyst to be in contact with the hydrogen and silicon tetrahalide is typically at least 0.01 seconds; alternatively at least 0.1 seconds; alternatively from 0.1 seconds to about 5 hours; alternatively from 0.1 seconds to about 45 minutes; alternatively from 0.1 seconds to about 5 minutes. Alternatively, there is no upper limit on the residence time for which Rxn step (i) is conducted. As used herein, "residence time" of Rxn step (i) means the time during which one reactor volume of copper catalyst makes contact with the hydrogen and halogenated silane monomers as copper catalyst passes through the reactor system in a continuous process or during which copper catalyst is placed within the reactor in a batch process. The desired residence time may be achieved by adjusting the copper catalyst flow rate in a continuous process or the duration of the step in a batch process.

The copper catalyst as used in step 5 or Rxn (i) of the method 1 is present in a sufficient amount. As used herein, a "sufficient amount" of copper catalyst means enough catalyst to form the silicon-containing copper catalyst, as described below, when the hydrogen and halogenated silane monomers make contact with the copper catalyst. For example, a sufficient amount of catalyst is at least 0.01 mg catalyst/cm$^3$ of the volume in the reactor system; alternatively at least 0.5 mg catalyst/cm$^3$ of the reactor volume; alternatively from 1 to 10,000 mg catalyst/cm$^3$ of the reactor volume.

The silicon-containing copper catalyst comprises at least 0.1% (w/w), alternatively from 0.1 to 90% (w/w), alternatively about 0.1% to about 55% (w/w), alternatively about 1% to about 20% (w/w), alternatively from about 1% to about 5% (w/w), of silicon based on the total weight of silicon-containing copper catalyst including any support if present. The percentage of silicon in the silicon-containing copper catalyst can be determined using standard analytical tests. For example, the percentage of silicon may be determined using inductively coupled plasma atomic emission spectroscopy (ICP-AES) and ICP mass spectrometry (ICP-MS).

Referring again to FIG. 1, in the second step 10 of the method 1, i.e., Rxn (ii), the silicon-containing copper catalyst makes contact with an organohalide at a temperature of from about 100° C. to about 600° C. to form at least one organohalosilane. The organohalide has the formula R'X', wherein R' is $C_1$-$C_{10}$ alkyl or $C_4$-$C_{10}$ cycloalkyl, and X' is a chloro, bromo, fluoro, or iodo group.

The alkyl groups represented by R' typically have from 1 to 10 carbon atoms, alternatively from 1 to 6 carbon atoms, alternatively from 1 to 4 carbon atoms. The cycloalkyl groups represented by R' typically have from 4 to 10 carbon atoms; alternatively 6 to 8 carbon atoms. Alkyl groups containing at least three carbon atoms can have a branched or unbranched structure. Examples of alkyl groups include, but are not limited to, methyl, ethyl, propyl, 1-methylethyl, butyl, 1-methylpropyl, 2-methylpropyl, 1,1-dimethylethyl, pentyl, 1-methylbutyl, 1-ethylpropyl, 2-methylbutyl, 3-methylbutyl, 1,2-dimethylpropyl, 2,2-dimethylpropyl, hexyl, heptyl, octyl, nonyl, and decyl. Examples of cycloalkyl groups include, but are not limited to, cyclobutyl, cyclopentyl, cyclohexyl, and methylcyclohexyl. Alternatively R' is a methyl group and X' is a chloro group. Specific examples of the organohalide include, but are not limited to, methyl chloride, methyl bromide, methyl iodide, ethyl chloride, ethyl bromide, ethyl iodide, cyclobutyl chloride, cyclobutyl bromide, cyclohexyl chloride, and cyclohexyl bromide.

One skilled in the art will understand that the reactor systems suitable for use in Rxn (ii) are similar to or the same as the reactor systems previously described for use in Rxn (i). The same reactor system may be used for Rxn (i) as used in Rxn (ii); however, separate or different reactor systems may also be used without exceeding the scope of the present disclosure. In such a reactor system, the organohalide typically makes contact with the silicon-containing copper catalyst by feeding the organohalide into the reactor that contains the silicon-containing copper catalyst produced in Rxn (i). The temperature at which the organohalide is allowed to make contact with the silicon-containing copper catalyst is typically from about 100° C. to about 600° C.; alternatively from about 200° C. to about 500° C.; alternatively from about 250° C. to about 375° C.

The residence time of the organohalide being in contact with the silicon-containing copper catalyst is sufficient for the organohalide to react with the silicon-containing copper catalyst to form an organohalosilane. The residence time for silicon-containing copper catalyst to be in contact with the organohalide is typically at least about 1 minute; alternatively at least about 5 minutes; alternatively from 1 minute to about 120 minutes; alternatively from 5 minutes to about 90 minutes; alternatively from 5 minutes to about 60 minutes. Alternatively, there is no upper limit on the residence time for which Rxn step (ii) is conducted. As used herein, "residence time" of Rxn step (ii) means the time in which one reactor volume of copper catalyst makes contact with the organohalide as this gas passes through the reactor system in a continuous process or that is placed within the reactor in a batch process. The desired residence time can be achieved by adjusting the flow rate of the organohalide or the duration of the step in a batch process.

The pressure at which the organohalide makes contact with the silicon-containing copper catalyst in Rxn (ii) can also be sub-atmospheric, atmospheric, or super-atmospheric. For example, the pressure is typically from about 100 to 2000 kilopascals gauge (kPag); alternatively from about 100 to about 1000 kPag; alternatively from about 100 to about 800 kPag.

The silicon-containing copper catalyst used in step 10 or Rxn (ii) of the method 1 is present in a "sufficient amount". As used herein, a "sufficient amount" of silicon-containing copper catalyst is enough catalyst to form the organohalosilane, described below, when contacted with the organohalide. For example, a sufficient amount of silicon-containing copper catalyst is at least 0.01 mg catalyst/cm$^3$ of reactor volume; alternatively at least 0.5 mg catalyst/cm$^3$ of reactor volume; alternatively from 1 to 10000 mg catalyst/cm$^3$ of reactor volume.

Rxn (ii) is typically conducted until the silicon in the silicon-containing copper catalyst is spent, e.g., falls below a predetermined limit. The predetermined limit for the amount of silicon in the silicon-containing catalyst at which Rxn (ii) is halted or suspended is typically less than 100% (w/w); alternatively, 90% (w/w) or less, alternatively less than about 75% (w/w), alternatively less than about 40% (w/w), of its initial weight percent, based on the total weight of catalyst including any support. As used herein, the "initial weight percent of silicon in the silicon-containing copper catalyst" means the weight percent of silicon in the silicon-containing copper catalyst before the silicon-containing copper catalyst is contacted with the organohalide in Rxn (ii). The amount of silicon in the silicon-containing copper catalyst can be monitored by correlating organohalosilane production or alternatively, diorganodihalosilane production, with the weight percent of silicon in the silicon-containing copper catalyst and then monitoring organohalosilane production or it may be determined as described above for the silicon-containing copper catalyst.

Step 5 [Rxn (i)] and step 10 [Rxn (ii)] of the method 1 are conducted separately and consecutively. As used herein, "separately" means that the Rxn (i) and Rxn (ii) do not overlap or coincide. As used herein, "consecutively" means that Rxn (ii) is performed after Rxn (i) in the method; however, additional steps may be performed between Rxn (i) and (ii), such as described below.

Referring once again to FIG. 1, the method 1 of the present disclosure may also include a third step 15 [Rxn (iii)] that occurs after Rxn (ii) is suspended or halted. This third step 15 [Rxn (iii)] involves repeating the first step 5 and second step 10 one or more times. Upon repeating the first step [Rxn (i)], the spent silicon-containing copper catalyst from Rxn (ii) is contacted with the mixture comprising hydrogen gas and halogenated silane monomers at a temperature of from 500° C. to 1400° C. to reform the silicon-containing copper catalyst comprising at least 0.1% (w/w) silicon. This reformed silicon-containing copper catalyst is then subjected to repeating the second step 10 [Rxn (ii)] by making contact with the organohalide at a temperature of from 100° C. to 600° C. to form at least one organohalosilane, or alternatively at least one diorganodihalosilane. This third step 15 [Rxn (iii)] may be performed at least 1 time, alternatively from 1 to 10$^5$ times, alternatively from 1 to 1000 times, alternatively from 1 to 100 times, alternatively from 1 to 10 times. One skilled in the art will understand that this third step 15 [Rxn (iii)] may be performed more than 1 time with no upper limit being placed on the number of times the step may be performed without exceeding the scope of the disclosure; alternatively, the upper limit may be determined according to commercial viability.

Still referring to FIG. 1, the method 1 may further comprise an intermediate step 20 of purging the reactor system prior to contacting the silicon-containing copper catalyst with the organohalide in the second step 10 [Rxn (ii)]. This intermediate purging step 20 may occur between Rxn (i) and Rxn (ii) either in conjunction with the initial performance of the first 5 and second 10 steps or upon repeating these two steps 5, 10 as part of the third step 15 [Rxn (iii)]. As used herein, "purging" means to introduce a gas stream to the reactor containing the silicon-containing copper catalyst to remove unwanted materials. Unwanted materials are, for example, $H_2$, $O_2$, and $H_2O$, among others. Purging may be accomplished with an inert gas, such as argon, or with a reactive gas, such as hydrogen.

If the organohalide or halogenated silane monomers are liquids at or below standard temperature and pressure, the method may further comprise pre-heating and gasifying the organohalide or halogenated silane monomers by any known method prior to contacting the silicon tetrahalide with the copper catalyst in Rxn (i) or contacting the organohalide with the silicon-containing copper catalyst in Rxn (ii). Alternatively, the process may further comprise the bubbling of hydrogen gas through the liquid halogenated silane monomers or organohalide in order to vaporize the halogenated silane monomers or organohalide prior to making contact with the copper catalyst in Rxn (i) and the silicon-containing copper catalyst in Rxn (ii), respectively.

Referring once again to FIG. 1, the method 1 may further comprise a fourth step 25 of recovering the organohalosilanes produced in Rxn (ii). The organohalosilanes may be recovered by, for example, removing gaseous organohalosilanes from the reactor system followed by isolation via distillation. According to one aspect of the present disclosure, the organohalosilane produced by the method 1 described and exemplified above is a diorganodihalosilane having the formula R"$_2$SiX"$_2$, wherein R" is a $C_1$-$C_{10}$ alkyl group or a $C_4$-$C_{10}$ cycloalkyl group, and X" is a fluoro, chloro, bromo, or iodo group. Several examples of diorganodihalosilanes prepared according to the present process include, but are not limited to, dimethyldichlorosilane (i.e., $(CH_3)_2SiCl_2$), dimethyldibromosilane, dimethyldiiodosilane, dimethyldifluorosilane, diethyldichlorosilane, diethyldibromo-silane, diethyldiiodosilane, dicyclohexyldichlorosilane, and dicyclohexyldibromo-silane. The method 1 may also produce other organohalosilanes or hydrohalosilanes, such as those having the formula R"$_a$HSiX"$_{(3-a)}$, R"SiX"$_3$, HSiX"$_3$, and R"$_3$SiX", where R" and X" are as defined above and subscript (a) is 1 or 2. Still referring to FIG. 1, the method may also include the additional step 30 of hydrolyzing the organohalosilane recovered in this fourth step 25 to produce polyorganosiloxanes for subsequent use in a variety of industries and applications. One skilled in the art will understand that such hydrolysis may be accomplished using any method or process known in the art capable of producing the desired polyorganosiloxane The following specific embodiments are given to illustrate the method of forming at least one organohalosilane according to the teachings of the present disclosure and should not be construed to limit the scope of the disclosure. Those skilled-in-the-art, in light of the present disclosure, will appreciate that many changes can be made in the specific embodiments which are disclosed herein and still obtain a like or similar result without departing from or exceeding the spirit or scope of the disclosure. One skilled in the art will further understand that any properties reported herein represent properties that are routinely measured and can be obtained by multiple different methods. The methods described herein represent one such method and other methods may be utilized without exceeding the scope of the present disclosure.

The following examples are presented to better illustrate the method of the present invention, but are not to be considered as limiting the invention, which is delineated in the appended claims. Unless otherwise noted, all parts and percentages reported in the examples are by weight. Table 1 lists several abbreviations used to indicate the identified terms throughout the following examples. The reaction system, reagents, product analysis, and flow rates used throughout the Examples are also summarized below.

The reaction system used in each of the Examples comprises a 4.8 mm inner diameter quartz glass tube in a flow reactor. The reactor tube is heated using a Lindberg/Blue Minimite 2.54 cm tube furnace. Omega FMA 5500 mass flow controllers are used to control gas flow rates. A stainless steel bubbler is used to introduce halogenated silane monomers into the $H_2$ gas stream. The amount of halogenated silane monomers in the $H_2$ gas stream is adjusted by changing the temperature of the halogenated silane monomers in the bubbler according to calculations using well-known thermodynamic principles. The reactor effluent passes through an actuated 6-way valve from Vici.

TABLE 1

List of abbreviations and terms used in the Examples.

| Abbreviation | Term |
|---|---|
| G | gram |
| Mg | milligram |
| Me | methyl |
| Wt | weight |
| % | percent |
| Mol | mole |
| hr | hour |
| ° C. | degrees Celsius |
| NA | Not Applicable |
| mL | milliliters |
| cm | centimeter |
| sccm | standard cubic centimeters per minute |
| TCD | thermal conductivity detector |
| Sel. | selectivity |
| MeSiCl$_3$ | methyltrichlorosilane |
| Me$_2$SiCl$_2$ | dimethyldichlorosilane |
| SiCl$_4$ | silicon tetrachloride |
| Me$_2$SiCl$_2$ | weight of dimethyldichlorosilane divided by the sum |
| Selectivity | of the weights all other volatile Si containing products |

TABLE 1-continued

List of abbreviations and terms used in the Examples.

| Abbreviation | Term |
|---|---|
| Me$_2$SiCl$_2$ wt. % | weight percent of Me$_2$SiCl$_2$ leaving the reactor based upon the total mass leaving the reactor |
| GC | gas chromatography |

The activated carbon and various metals or metal salts, as well as all other reagents used in the Examples are purchased from Sigma Aldrich, Milwaukee, Wis. The effluent of the reactor system containing the products and by-products are analyzed using gas chromatography (GC). The flow rate ratios are determined using known thermodynamic principles using the flow rates, at standard temperature and pressure, for the hydrogen gas, halogenated silane monomers, and organohalide.

Example 1

Production of Methylchlorosilanes Using Copper Catalyst Treated at 750° C. with $H_2$/SiCl$_4$ at Different Ratios of $H_2$:SiCl$_4$ A copper catalyst (0.5 grams) comprising an activated carbon supported mixture of copper, gold and magnesium, prepared by incipient wetness impregnation, is treated with $H_2$/SiCl$_4$ for 30 min at 750° C.-950° C. by bubbling $H_2$ through a stainless steel SiCl$_4$ bubbler. The total flow of $H_2$ and SiCl$_4$ is 150 sccm and the mole ratio of $H_2$ to SiCl$_4$ is varied from 4:1 to 1:1. The SiCl$_4$ flow is controlled by $H_2$ flow by varying the bubbler temperature between 14.6° C. to 37.2° C. The gas and vapor leaving the bubbler is fed into the glass tube of a flow reactor containing the copper catalyst to form a silicon-containing copper catalyst comprising from 24-47% (w/w) Si. After 30 minutes, the SiCl$_4$ flow is ceased and a hydrogen flow of 100 sccm is maintained while cooling to 300° C. over a period of 1 hour. When the reactor reached 300° C., all $H_2$ was purged from the reactor and catalyst with an argon flow of 50 sccm for 30 min. After 30 min, the argon flow is ceased, and CH$_3$Cl is fed through the reactor at a flow rate of 5 sccm, 300° C., and atmospheric pressure for 60 min. The reaction is periodically sampled and analyzed by gas chromatography to determine the weight percent (CH$_3$)$_2$SiCl$_2$, based on the total mass leaving the reactor.

Next, the CH$_3$Cl feed is ceased, and the copper catalyst treated with $H_2$ at 500° C. for 30-60 min and contacted again with $H_2$/SiCl$_4$, to reform the silicon-containing copper catalyst, for 30 min at 750° C.-950° C. The combined flow rate of $H_2$ and SiCl$_4$ is 150 sccm, and the mole ratio of $H_2$ to SiCl$_4$ is varied from 4:1 to 1:1. After the silicon-containing copper catalyst is reformed, it is purged with argon, again, and CH$_3$Cl is contacted with the reformed silicon-contained copper catalyst as described above. The cycle was repeated ~20 times by varying $H_2$ to SiCl$_4$ ratios from 4:1 to 1:1. The amount of Si deposited on the catalyst ranges from 24-44% in the first step Rxn (i) at 750° C. and the amount of Si removed from the deposited Si is 3-8% in second step Rxn (ii) depending on the $H_2$ to SiCl$_4$ ratios. The cumulative selectivity towards Me$_2$SiCl$_2$ in step 2 is 55% irrespective of $H_2$ to SiCl$_4$ ratios. At 950° C., the amount of Si deposited on the catalyst ranges from 27-47% in the first step Rxn (i) and the amount of Si removed from the deposited Si is 2-7% in the second step Rxn (ii) depending on the $H_2$ to SiCl$_4$ ratios. The cumulative selectivity towards Me$_2$SiCl$_2$ in step 2 is 56% irrespective of $H_2$ to SiCl$_4$ ratios. This example demonstrates that dimethyldichlorosilane is produced by the method of the present disclosure and the silicon deposition on the catalyst is increased with decrease in $H_2$ partial pressure (increase in $SiCl_4$ partial pressure).

Example 2

Production of Methylchlorosilanes Using Copper Catalyst Treated at 750° C. with $H_2/HSiCl_3$ A copper catalyst (0.5 grams) comprising an activated carbon supported mixture of copper, gold and magnesium, prepared by incipient wetness impregnation, is treated in $H_2/HSiCl_3$ for 30 min at 750° C. by bubbling $H_2$ through a stainless steel $HSiCl_3$ bubbler at −7.6° C. The total flow of $H_2$ and $HSiCl_3$ is 150 sccm and the mole ratio of $H_2$ to $HSiCl_3$ is 4:1. The gas and vapor leaving the bubbler is fed into the glass tube of a flow reactor containing the copper catalyst to form a silicon-containing copper catalyst up to 43% (w/w) Si. After 30 minutes, the $HSiCl_3$ flow is ceased and a hydrogen flow of 100 sccm is maintained while cooling to 300° C. over a period of 1 hour. When the reactor reached 300° C., all $H_2$ is purged from the reactor and catalyst with an argon flow of 50 sccm for 30 min. After 30 min, the argon flow is ceased, and $CH_3Cl$ is fed through the reactor at a flow rate of 5 sccm, 300° C. and atmospheric pressure. The reaction is periodically sampled and analyzed by gas chromatography to determine the weight percent $(CH_3)_2SiCl_2$, based on the total mass leaving the reactor.

Next, the $CH_3Cl$ feed is ceased, and the copper catalyst is treated with $H_2$ at 500° C. for 30-60 min and contacted again with $H_2/HSiCl_3$, to reform the silicon-containing copper catalyst, for 30 min at 750° C. The combined flow rate of $H_2$ and $HSiCl_3$ is 150 sccm, and the mole ratio of $H_2$ to $HSiCl_3$ is 4:1. After the silicon-containing copper catalyst is reformed, it is purged with argon, again, and $CH_3Cl$ is contacted with the reformed silicon-contained copper catalyst as described above. The cycle is repeated 5 times and the amount of Si deposited on the catalyst is 43% in the first step Rxn (i) at 750° C. and the amount of Si removed from the deposited Si is 16% in the second step Rxn (ii) at 300° C. The cumulative selectivity of $Me_2SiCl_2$ obtained is about 60% in the second step Rxn (ii). This example demonstrates that dimethyldichlorosilane is produced by the method of the present disclosure and the silicon conversion is increased with $HSiCl_3$ feed compared with $SiCl_4$ feed.

Example 3

Production of Methylchlorosilanes Using Copper Catalyst Treated at 750-950° C. with $H_2/CH_3SiCl_3$ A copper catalyst (0.5 grams) comprising an activated carbon supported mixture of copper, gold and magnesium, prepared by incipient wetness impregnation, is treated in $H_2/CH_3SiCl_3$ for 30 min at 750° C.-950° C. by bubbling $H_2$ through a stainless steel $CH_3SiCl_3$ bubbler at 21.9° C. The total flow of $H_2$ and $CH_3SiCl_3$ is 150 sccm and the mole ratio of $H_2$ to $CH_3SiCl_3$ is 4:1. The gas and vapor leaving the bubbler is fed into the glass tube of a flow reactor containing the copper catalyst to form a silicon-containing copper catalyst up to 3% (w/w) Si. After 30 minutes, the $CH_3SiCl_3$ flow is ceased and a hydrogen flow of 100 sccm is maintained while cooling to 300° C. over a period of 1 hour. When the reactor reached 300° C., all $H_2$ is purged from the reactor and catalyst with an argon flow of 50 sccm for 30 min. After 30 min, the argon flow is ceased, and $CH_3Cl$ is fed through the reactor at a flow rate of 5 sccm, 300° C. and atmospheric pressure for 60 min. The reaction is periodically sampled and analyzed by gas chromatography to determine the weight percent $(CH_3)_2SiCl_2$, based on the total mass leaving the reactor.

Next, the $CH_3Cl$ feed is ceased, and the copper catalyst is treated with $H_2$ at 500° C. for 30-60 min and contacted again with $H_2/CH_3SiCl_3$, to reform the silicon containing copper catalyst, for 30 min at 750° C. The combined flow rate of $H_2$ and $CH_3SiCl_3$ is 150 sccm, and the mole ratio of $H_2$ to $CH_3SiCl_3$ is 4:1. After the silicon-containing copper catalyst is reformed, it is purged with argon, again, and $CH_3Cl$ is contacted with the reformed silicon-contained copper catalyst as described above. The cycle is repeated 6 times by varying the first step Rxn (i) reaction temperature at 750° C. and 950° C. The selectivity of $Me_2SiCl_2$ is high (65%) in the second step Rxn (ii) when the first step Rxn (i) is carried out at 950° C. compared to 750° C. (40%). This example demonstrates that dimethyldichlorosilane is produced by the method of the present disclosure.

Example 4

Production of Methylchlorosilanes Using Copper Catalyst Treated at 750° C. with $H_2$ and a Mixture of $HSiCl_3$ and $SiCl_4$ A copper catalyst (0.5 grams) comprising an activated carbon supported mixture of copper, gold and magnesium, prepared by incipient wetness impregnation, is treated with a mixture of $HSiCl_3$ and $SiCl_4$ along with $H_2$ for 30 min at 750° C. The mixture of chlorosilanes ($HSiCl_3+SiCl_4$) is fed in to the reactor using a syringe pump and the $H_2$ gas through a mass flow controller. The total flow of $H_2$ and chlorosilanes is 150 sccm and the mole ratio of $H_2$ to chlorosilanes is 4:1. The reaction is studied at different ratios of $SiCl_4$ to $HSiCl_3$. The gas and vapor is fed into the glass tube of a flow reactor containing the copper catalyst to form a silicon-containing copper catalyst compromising from 33-45% (w/w) Si. After 30 minutes, the chlorosilanes feed is ceased and a hydrogen flow of 100 sccm is maintained while cooling to 300° C. over a period of 1 hour. When the reactor reached 300° C., all $H_2$ is purged from the reactor and catalyst with an argon flow of 50 sccm for 30 min. After 30 min, the argon flow is ceased, and $CH_3Cl$ is fed through the reactor at a flow rate of 5 sccm, 300° C. and atmospheric pressure for 60 min. The reaction is periodically sampled and analyzed by gas chromatography to determine the weight percent $(CH_3)_2SiCl_2$, based on the total mass leaving the reactor.

Next, the $CH_3Cl$ feed is ceased, and the copper catalyst is treated with $H_2$ at 500° C. for 30-60 min and contacted again with $H_2/(HSiCl_3+SiCl_4)$, to reform the silicon-containing copper catalyst, for 30 min at 750° C. The combined flow rate of $H_2$ and $(HSiCl_3+SiCl_4)$ is 150 sccm, and the mole ratio of $H_2$ to $(HSiCl_3+SiCl_4)$ is 4:1. After the silicon-containing copper catalyst is reformed, it is purged with argon, again, and $CH_3Cl$ is contacted with the reformed silicon-contained copper catalyst as described above. The cycle is repeated 15 times by varying the feed ratio $(HSiCl_3:SiCl_4)$ in the first step Rxn (i). The cumulative selectivity towards $Me_2SiCl_2$ obtained is about 57% in the second step Rxn (ii). This example demonstrates that dimethyldichlorosilane is produced by the method of the present disclosure.

Example 5

Production of Methylchlorosilanes Using Copper Catalyst Treated at 750° C. with $H_2$ and a Mixture of $CH_3SiCl_3$ and $SiCl_4$ A copper catalyst (0.5 grams) comprising an activated carbon supported mixture of copper, gold and magnesium, prepared by incipient wetness impregnation, is treated with a mixture of $CH_3SiCl_3$ and $SiCl_4$ along with $H_2$ for 30 min at 750° C. The mixture of chlorosilanes ($CH_3SiCl_3+SiCl_4$) is fed in to the reactor using a syringe pump and the $H_2$ gas through a mass flow controller. The total flow of $H_2$ and chlorosilanes is 150 sccm and the mole ratio of $H_2$ to chlorosilanes is 4:1. The reaction is studied at different ratios of $SiCl_4$ to $CH_3SiCl_3$. The gas and vapor is fed into the glass tube of a flow reactor containing the copper catalyst to form a silicon-containing copper catalyst compromising from 10-24% (w/w) Si. After 30 minutes, the chlorosilanes feed is ceased and a hydrogen flow of 100 sccm is maintained while cooling to 300° C. over a period of 1 hour. When the reactor reached 300° C., all $H_2$ is purged from the reactor and catalyst with an argon flow of 50 sccm for 30 min. After 30 min, the argon flow is ceased, and $CH_3Cl$ is fed through the reactor at a flow rate of 5 sccm, 300° C. and atmospheric pressure for 60 min. The reaction is periodically sampled and analyzed by gas chromatography to determine the weight percent $(CH_3)_2SiCl_2$, based on the total mass leaving the reactor.

Next, the $CH_3Cl$ feed is ceased, and the copper catalyst is treated with $H_2$ at 500° C. for 30-60 min and contacted again with $H_2/(CH_3SiCl_3+SiCl_4)$, to reform the silicon-containing copper catalyst, for 30 min at 750° C. The combined flow rate of $H_2$ and $(CH_3SiCl_3+SiCl_4)$ is 150 sccm, and the mole ratio of $H_2$ to $(CH_3SiCl_3+SiCl_4)$ is 4:1. After the silicon-containing copper catalyst is reformed, it is purged with argon, again, and $CH_3Cl$ is contacted with the reformed silicon-contained copper catalyst as described above. The cycle is repeated 6 times by varying the feed ratio ($MeSiCl_3:SiCl_4$) in the first step Rxn (i). The cumulative selectivity towards $Me_2SiCl_2$ obtained is about 48% in the second step Rxn (ii). This example demonstrates that dimethyldichlorosilane is produced by the method of the present disclosure

Example 6

Production of Methylchlorosilanes Using Copper Catalyst Treated at 750° C. with $H_2$ and a Mixture of $HSiCl_3$, $CH_3SiCl_3$ and $SiCl_4$ A Copper catalyst (0.5 grams) comprising an activated carbon supported mixture of copper, gold and magnesium, prepared by incipient wetness impregnation, is treated with a mixture of $CH_3SiCl_3$, $HSiCl_3$, and $SiCl_4$ along with $H_2$ for 30 min at 750° C. The mixture of chlorosilanes ($HSiCl_3+CH_3SiCl_3+SiCl_4$) is fed in to the reactor using a syringe pump and the $H_2$ gas through a mass flow controller. The total flow of $H_2$ and chlorosilanes is 150 sccm and the mole ratio of $H_2$ to chlorosilanes is 4:1. The reaction is studied at different ratios of $SiCl_4/HSiCl_3/CH_3SiCl_3$. The gas and vapor is fed into the glass tube of a flow reactor containing the copper catalyst to form a silicon-containing copper catalyst compromising from 15-30% (w/w) Si. After 30 minutes, the chlorosilanes feed is ceased and a hydrogen flow of 100 sccm is maintained while cooling to 300° C. over a period of 1 hour. When the reactor reaches 300° C., all $H_2$ is purged from the reactor and catalyst with an argon flow of 50 sccm for 30 min. After 30 min, the argon flow is ceased, and $CH_3Cl$ is fed through the reactor at a flow rate of 5 sccm, 300° C. and atmospheric pressure for 60 min. The reaction is periodically sampled and analyzed by gas chromatography to determine the weight percent $(CH_3)_2SiCl_2$, based on the total mass leaving the reactor.

Next, the $CH_3Cl$ feed is ceased, and the copper catalyst is treated with $H_2$ at 500° C. for 30-60 min and contacted again with $H_2/(HSiCl_3+CH_3SiCl_3+SiCl_4)$, to reform the silicon containing copper catalyst, for 30 min at 750° C. The combined flow rate of $H_2$ and $(HSiCl_3+CH_3SiCl_3+SiCl_4)$ is 150 sccm, and the mole ratio of $H_2$ to $(HSiCl_3+CH_3SiCl_3+SiCl_4)$ is 4:1. After the silicon-containing copper catalyst is reformed, it was purged with argon, again, and $CH_3Cl$ is contacted with the reformed silicon-contained copper catalyst as described above. The cycle is repeated 8 times by varying the feed ratio ($SiCl_4:HSiCl_3:MeSiCl_3$) in the first step Rxn (i). The cumulative selectivity towards $Me_2SiCl_2$ obtained is about 37% in the second step Rxn (ii).

Example 7

Production of Methylchlorosilanes Over Copper Silicide Catalyst Treated at 750° C. with $H_2$ and a Mixture of $HSiCl_3$ and $SiCl_4$ An unsupported copper catalyst (Copper silicide, $Cu_5Si$, 6.15 grams) comprising 92 wt. % copper is treated with a mixture of $HSiCl_3$ and $SiCl_4$ along with $H_2$ by varying reaction time and the composition of chlorosilanes at 750° C. [$1^{st}$ step, Rxn (i)]. The mixture of chlorosilanes ($HSiCl_3+SiCl_4$) is fed in to the reactor using a syringe pump and the $H_2$ gas through a mass flow controller. The total flow of $H_2$ and chlorosilanes is 150 sccm and the mole ratio of $H_2$ to chlorosilanes is 1:1. The reaction is studied at different ratios of $SiCl_4$ to $HSiCl_3$.

The gas and vapor is fed into the glass tube of a flow reactor containing the copper catalyst to form a silicon-containing copper catalyst with up to 45% (w/w) Si. After reacting with chlorosilanes and $H_2$, the chlorosilanes feed is ceased and a hydrogen flow of 100 sccm is maintained while cooling to 320° C. over a period of 1 hour. When the reactor reaches 320° C., all $H_2$ is purged from the reactor and catalyst with argon at a flow rate of 50 sccm for 30 minutes. After 30 minutes, the argon flow is ceased, and $CH_3Cl$ is fed through the reactor at a flow rate of 5 sccm, 320° C., and atmospheric pressure for 60 minutes [$2^{nd}$ step, Rxn (ii)]. The reaction is periodically sampled and analyzed by gas chromatography to determine the weight percent $(CH_3)_2SiCl_2$, based on the total mass leaving the reactor.

The $CH_3Cl$ feed is then ceased, and the copper catalyst is treated with $H_2$ at 500° C. for 30-60 min and contacted again with $H_2/(HSiCl_3+SiCl_4)$, to reform the silicon containing copper catalyst at 750° C. The combined flow rate of $H_2$ and $(HSiCl_3+SiCl_4)$ is 150 sccm, and the mole ratio of $H_2$ to $(HSiCl_3+SiCl_4)$ is 1:1. After the silicon-containing copper catalyst is reformed, it is purged with argon again, and $CH_3Cl$ is contacted with the reformed silicon-contained copper catalyst as described above. A total of 27 cycles are carried out by varying chlorosilanes composition and reaction times. The results are shown in Table 2. This example demonstrates that dimethyldichlorosilane is produced by the method of the present disclosure.

TABLE 2

Reaction Results

| Cycle | Step1 Time (min) | SiCl$_4$:HSiCl$_3$ ratio | Si Removed, Step2 (mg) | Selectivity of Me$_2$SiCl$_2$ | Selectivity of MeSiCl$_3$ | Selectivity of others |
|---|---|---|---|---|---|---|
| 1 | 4 | 80:20 | 8 | 56% | 25% | 19% |
| 2 | 4 | 95:5 | 10 | 62% | 26% | 12% |
| 3 | 4 | 95:5 | 11 | 61% | 22% | 17% |
| 4 | 4 | 80:20 | 9 | 52% | 24% | 24% |
| 5 | 8 | 90:10 | 14 | 52% | 22% | 26% |
| 6 | 16 | 80:20 | 38 | 18% | 11% | 71% |
| 7 | 6 | 90:10 | 3 | 47% | 32% | 21% |
| 8 | 16 | 95:5 | 4 | 40% | 24% | 36% |
| 9 | 4 | 90:10 | 5 | 29% | 19% | 52% |
| 10 | 8 | 80:20 | 6 | 58% | 30% | 11% |
| 11 | 8 | 80:20 | 5 | 36% | 26% | 38% |
| 12 | 8 | 90:10 | 9 | 62% | 28% | 10% |
| 13 | 16 | 90:10 | 13 | 65% | 22% | 13% |
| 14 | 16 | 80:20 | 21 | 68% | 16% | 16% |
| 15 | 16 | 90:10 | 75 | 73% | 15% | 12% |
| 16 | 16 | 95:5 | 37 | 58% | 28% | 14% |
| 17 | 4 | 90:10 | 1 | 56% | 12% | 32% |
| 18 | 16 | 80:20 | 27 | 72% | 14% | 14% |
| 19 | 16 | 90:10 | 20 | 40% | 16% | 43% |
| 20 | 4 | 80:20 | 9 | 25% | 18% | 58% |
| 21 | 4 | 95:5 | 7 | 54% | 23% | 23% |
| 22 | 8 | 90:10 | 7 | 53% | 29% | 18% |
| 23 | 8 | 95:5 | 13 | 66% | 22% | 12% |
| 24 | 8 | 95:5 | 9 | 63% | 28% | 9% |
| 25 | 16 | 95:5 | 8 | 61% | 26% | 13% |
| 26 | 8 | 80:20 | 11 | 51% | 22% | 27% |
| 27 | 8 | 95:5 | 15 | 29% | 14% | 57% |

Example 8

Production of Methylchlorosilanes Over Metallic Copper Catalyst Treated at 750° C. with H$_2$ and a Mixture of HSiCl$_3$ and SiCl$_4$ An unsupported metallic copper catalyst (4 grams) comprising 100% copper is treated with a mixture of HSiCl$_3$ and SiCl$_4$ along with H$_2$ at 750° C. [1$^{st}$ step, Rxn (i)] for 30 min. The mixture of chlorosilanes (HSiCl$_3$+SiCl$_4$) is fed in to the reactor using a syringe pump and the H$_2$ gas through a mass flow controller. The total flow of H$_2$ and chlorosilanes is 150 sccm and the mole ratio of H$_2$ to chlorosilanes is 1:1. The reaction is studied at a ratio of 70:30 of SiCl$_4$ to HSiCl$_3$. The gas and vapor is fed into the glass tube of a flow reactor containing the copper catalyst to form a silicon-containing copper catalyst with up to 20% (w/w) Si. After reacting with chlorosilanes and H$_2$, the chlorosilanes feed is ceased and a hydrogen flow of 100 sccm is maintained while cooling to 320° C. over a period of 1 hour. When the reactor reaches 320° C., all H$_2$ is purged from the reactor and catalyst with argon at a flow rate of 50 sccm for 30 min. After 30 minutes, the argon flow is ceased, and CH$_3$Cl is fed through the reactor at a flow rate of 5 sccm, 320° C., and atmospheric pressure for 60 minutes [2$^{nd}$ step, Rxn (ii)].

The reaction is periodically sampled and analyzed by gas chromatography to determine the weight percent (CH$_3$)$_2$SiCl$_2$, based on the total mass leaving the reactor. The reaction produced approximately 40 mg of reactive Si with 70% selectivity towards Me$_2$SiCl$_2$, 24% of MeSiCl$_3$, and 6% other methylchlorosilanes. This Example demonstrates that dimethyldichlorosilane is produced by the method of the present disclosure.

Example 9

Production of Methylchlorosilanes Over Silica Supported Nickel Catalyst Treated at 750° C. with H$_2$ and a Mixture of HSiCl$_3$ and SiCl$_4$ A total of 14 grams of silica gel is impregnated with 29.72 grams of Ni(NO$_3$)$_2$ dispersed in 50 ml de-ionized water. The resultant mixture is placed on a hot plate to remove excess solvent. The material is dried in a hot air oven at 200° C. for 12 hours and then calcined at 500° C. for 6 hours in air oven.

The gas phase activity of this catalyst is evaluated using a fixed bed reactor. In a typical experiment, about 1 gram of catalyst is reduced under H$_2$ at 500° C. at a flow rate of 100 sccm for 3-4 hours; then treated with a mixture of HSiCl$_3$ and SiCl$_4$ along with H$_2$ at 750° C. [1$^{st}$ step, Rxn (i)] for 30 minutes. The mixture of chlorosilanes (HSiCl$_3$+SiCl$_4$) is fed in to the reactor using a syringe pump and the H$_2$ gas through a mass flow controller. The total flow of H$_2$ and chlorosilanes is 150 sccm and the mole ratio of H$_2$ to chlorosilanes is 1:1.

The reaction is studied at a ratio of 70:30 of SiCl$_4$ to HSiCl$_3$. The gas and vapor is fed into the glass tube of a flow reactor containing the nickel catalyst to form a silicon-containing nickel catalyst with up to 40% (w/w) Si. After reacting with chlorosilanes and H$_2$, the chlorosilanes feed is ceased and a hydrogen flow rate of 100 sccm is maintained while cooling to 320° C. over a period of 1 hour. When the reactor reaches 320° C., all H$_2$ is purged from the reactor and catalyst using argon at a flow rate of 50 sccm for 30 minutes. After 30 minutes, the argon flow is ceased, and CH$_3$Cl is fed through the reactor at a flow rate of 5 sccm, 320° C., and atmospheric pressure for 60 minutes [2$^{nd}$ step, Rxn (ii)].

The reaction is periodically sampled and analyzed by gas chromatography to determine the weight percent (CH$_3$)$_2$SiCl$_2$, based on the total mass leaving the reactor. The reaction produces approximately 5% selectivity towards Me$_2$SiCl$_2$, 30% of MeSiCl$_3$, and 65% other methylchlorosilanes. This Example demonstrates that dimethyldichlorosilane is produced by the method of the present disclosure.

Example 10

Production of Methylchlorosilanes Over Copper-Nickel Bimetallic Catalyst Treated at 750° C. with H$_2$ and a Mixture of HSiCl$_3$ and SiCl$_4$ About 1 gram of catalyst comprising silica supported mixture of copper and nickel, prepared by incipient wetness impregnation is treated with a mixture of HSiCl$_3$ and SiCl$_4$ along with H$_2$ for 30 minutes at 750° C. The mixture of chlorosilanes (HSiCl$_3$+SiCl$_4$) is fed in to the reactor using a syringe pump and the H$_2$ gas through a mass flow controller. The total flow of H$_2$ and chlorosilanes is 150 sccm and the mole ratio of H$_2$ to chlorosilanes is 1:1. The gas and vapor is fed into the glass tube of a flow reactor containing the copper & nickel catalyst to form a silicon-containing copper catalyst with up to 45% (w/w) Si. After 30 minutes, the chlorosilanes feed is ceased and a hydrogen flow rate of 100 sccm is maintained while cooling to 320° C. over a period of 1 hour. When the reactor reaches 320° C., all H$_2$ is purged from the reactor and catalyst with argon at a flow rate of 50 sccm for 30 minutes. After 30 minutes, the argon flow is ceased, and CH$_3$Cl is fed through the reactor at a flow rate of 5 sccm, 320° C., and atmospheric pressure for 60 minutes. The reaction is periodically sampled and analyzed by gas chromatography to determine the weight percent (CH$_3$)$_2$SiCl$_2$, based on the total mass leaving the reactor. The reaction produces approximately 20 mg of reactive Si with 30% selectivity towards Me$_2$SiCl$_2$, 30% of MeSiCl$_3$, and 40% other methylchlorosilanes. This Example demonstrates that dimethyldichlorosilane is produced by the method of the present disclosure.

The foregoing description of various forms of the invention has been presented for purposes of illustration and description. It is not intended to be exhaustive or to limit the invention to the precise forms disclosed. Numerous modifications or variations are possible in light of the above teachings. The forms discussed were chosen and described to provide the best illustration of the principles of the invention and its practical application to thereby enable one of ordinary skill in the art to utilize the invention in various forms and with various modifications as are suited to the particular use contemplated. All such modifications and variations are within the scope of the invention as determined by the appended claims when interpreted in accordance with the breadth to which they are fairly, legally, and equitably entitled.

That which is claimed is:

1. A method of preparing at least one organohalosilane, the method comprising the following separate and consecutive steps:
    a first step [Rxn (i)] of contacting a copper catalyst with a mixture comprising hydrogen (H2) gas and one or more halogenated silane monomers; wherein the residence time of the copper catalyst being in contact with the hydrogen gas and halogenated silane monomers is from 0.1 second to 45 minutes at a temperature between 500° C. and 950° C. to form a silicon-containing copper catalyst comprising at least 0.1% (w/w) of silicon; and
    a second step [Rxn (ii)] of contacting the silicon-containing copper catalyst with an organohalide at a temperature of from 100° C. to 600° C. to form at least one organohalosilane;
    wherein the halogenated silane monomers include RSiX3, HSiX3, or a mixture thereof; and optionally with SiX4 being added thereto, such that R is an alkyl group having between 1 to 10 carbon atoms and X is independently selected as a chloro, bromo, fluoro, or iodo group;
    wherein the copper catalyst is selected from copper and a mixture comprising copper and at least one element selected from gold, magnesium, calcium, cesium, tin, nickel, and sulfur; and
    wherein the organohalosilane is a diorganodihalosilane.

2. The method of claim 1, wherein the optional SiX4 added as part of the halogenated silane monomers is silicon tetrachloride.

3. The method of claim 1, further comprising a third step [Rxn(iii)] in which the separate and consecutive first and second steps are repeated one or more times.

4. A method of preparing at least one organohalosilane, the method comprising the following separate and consecutive steps:
    a first step [Rxn (i)] of contacting a copper catalyst with a mixture comprising hydrogen (H2) gas and one or more halogenated silane monomers at a temperature of from 500° C. to 1400° C. to form a silicon-containing copper catalyst comprising at least 0.1% (w/w) of silicon; and
a second step [Rxn (ii)] of contacting the silicon-containing copper catalyst with an organohalide at a temperature of from 100° C. to 600° C. to form at least one organohalosilane;
    wherein the halogenated silane monomers include RSiX3, HSiX3, or a mixture thereof; and optionally with SiX4 being added thereto, such that R is an alkyl group having between 1 to 10 carbon atoms and X is independently selected as a chloro, bromo, fluoro, or iodo group;
    wherein the copper catalyst is selected from copper and a mixture comprising copper and at least one element selected from gold, magnesium, calcium, cesium, tin, nickel, and sulfur; and
    wherein the organohalosilane is a diorganodihalosilane; and
purging the silicon-containing copper catalyst formed in Rxn (i) with at least one of hydrogen gas or an inert gas prior to the contacting said catalyst with the organohalide in Rxn (ii).

5. The method according to claim 4, wherein the silicon-containing copper catalyst is first purged with hydrogen gas and then subsequently purged with an inert gas.

6. The method of claim 1, wherein the copper catalyst comprises copper in an amount between 0.1 to 80% (w/w) of the total weight of the catalyst.

7. The method of claim 1, wherein the copper catalyst further includes a metal oxide or carbon-based support.

8. The method of claim 1, wherein the copper catalyst comprises copper and nickel.

9. The method according to claim 6, wherein the support is activated carbon.

10. The method of claim 1, wherein the silicon-containing copper catalyst formed in Rxn (i) comprises from 0.1 to 55% (w/w) of silicon based on the total weight of the silicon-containing copper catalyst.

11. The method of claim 1, wherein the mole ratio of hydrogen gas to halogenated silane monomers including any optional SiX4 is from 10:1 to 1:1.

12. The method of claim 1, wherein in the halogenated silane monomers, the R is a methyl group and X is a chloro group.

13. The method of claim 1, wherein the organohalide has the formula R'X', where R' is a C1-C10 alkyl group or a C4-C10 cycloalkyl group, and X' is a chloro, bromo, fluoro, or iodo group.

14. The method of claim 13, wherein R' is a methyl group and X' is a chloro group.

15. The method of claim 1, wherein the organohalosilane has the formula R"2SiX"2, where R" is a C1-C10 alkyl group or a C4-C10 cycloalkyl group, and X" is a fluoro, chloro, bromo, or iodo group.

16. The method according to claim 15, wherein R" is a methyl group and X" is a chloro group.

17. The method of claim 1, further comprising the step of recovering the organohalosilane.

18. A method comprising the following separate and consecutive steps:
    a first step [Rxn (i)] of contacting a copper catalyst with a mixture comprising hydrogen (H2) gas and one or more halogenated silane monomers; wherein the residence time of the copper catalyst being in contact with the hydrogen gas and halogenated silane monomers is from 0.1 second to 45 minutes at a temperature between 500° C. and 950° C. to form a silicon-containing copper catalyst comprising at least 0.1% (w/w) of silicon; and
    a second step [Rxn (ii)] of contacting the silicon-containing copper catalyst with an organohalide at a temperature of from 100° C. to 600° C. to form at least one organohalosilane;
    wherein the halogenated silane monomers include RSiX3, HSiX3, or a mixture thereof; and optionally with SiX4 being added thereto, such that R is an alkyl group having between 1 to 10 carbon atoms and X is independently selected as a chloro, bromo, fluoro, or iodo group;

wherein the copper catalyst is selected from copper and a mixture comprising copper and at least one element selected from gold, magnesium, calcium, cesium, tin, nickel, and sulfur, and wherein the organohalosilane is a diorganodihalosilane;

wherein the method further comprises the step of hydrolyzing the organohalosilane to form a polyorganosiloxane.

\* \* \* \* \*